(12) United States Patent
Neumann

(10) Patent No.: US 11,935,642 B2
(45) Date of Patent: Mar. 19, 2024

(54) SYSTEM AND METHOD FOR GENERATING A NEONATAL DISORDER NOURISHMENT PROGRAM

(71) Applicant: KPN INNOVATIONS, LLC., Lakewood, CO (US)

(72) Inventor: Kenneth Neumann, Lakewood, CO (US)

(73) Assignee: KPN Innovations, LLC, Lakewood, CO (US)

( * ) Notice: Subject to any disclaimer, the term of this patent is extended or adjusted under 35 U.S.C. 154(b) by 301 days.

(21) Appl. No.: 17/187,970

(22) Filed: Mar. 1, 2021

(65) Prior Publication Data
US 2022/0277827 A1    Sep. 1, 2022

(51) Int. Cl.
*A61B 5/00*    (2006.01)
*G16H 10/60*   (2018.01)
(Continued)

(52) U.S. Cl.
CPC .......... *G16H 20/60* (2018.01); *A61B 5/4842* (2013.01); *A61B 5/7267* (2013.01); *G16H 10/60* (2018.01);
(Continued)

(58) Field of Classification Search
CPC ........ G16H 20/60; G16H 10/60; G16H 50/30; A61B 5/4842; A61B 5/7267; A61B 2503/045
See application file for complete search history.

(56) References Cited

U.S. PATENT DOCUMENTS 7,074,183 B2   7/2006   Castellanos
7,970,620 B2   6/2011   Brown
(Continued)

FOREIGN PATENT DOCUMENTS

CN    103751874 A   *   4/2014
RU    2691145 C2       6/2019
(Continued)

OTHER PUBLICATIONS

Title: A Brief Tool to Assess Image-Based Dietary Records and Guide Nutrition Counselling Among Pregnant Women: An Evaluation; JMIR MHealth and UHealth vol. 4 Issue: 4 Article No. e123 Published: Oct.-Dec. 2016; By: Ashman.
(Continued)

*Primary Examiner* — George R Evanisko
(74) *Attorney, Agent, or Firm* — Caldwell Intellectual Property Law

(57) ABSTRACT

A system and method for generating a neonatal disorder nourishment program comprising a computing device, the computing device configured to obtain a neonatal indicator element, identify a neonatal bundle as a function of the neonatal indicator element, produce a neonatal profile as a function of the neonatal bundle, wherein producing further comprises obtaining a neonatal functional goal as a function of the neonatal bundle, receiving a neonatal recommendation as a function of a neonatal database, and producing the neonatal profile as a function of the neonatal functional goal and neonatal recommendation using a neonatal machine-learning model, determine an aliment as a function of the neonatal profile, and generate a nourishment program as a function of the aliment.

20 Claims, 7 Drawing Sheets

(51) Int. Cl.
  *G16H 20/60* (2018.01)
  *G16H 50/30* (2018.01)

(52) U.S. Cl.
  CPC ........ *G16H 50/30* (2018.01); *A61B 2503/045* (2013.01)

(56) References Cited

U.S. PATENT DOCUMENTS

| | | | |
|---|---|---|---|
| 8,226,414 | B2 | 7/2012 | Bodin |
| 8,560,336 | B2 | 10/2013 | Schwarzberg |
| 8,684,922 | B2 | 4/2014 | Tran |
| 9,495,514 | B2 * | 11/2016 | McNair ................ G16H 50/50 |
| 10,373,522 | B2 | 8/2019 | Byron |
| 2002/0046060 | A1 | 4/2002 | Hoskyns |
| 2006/0074279 | A1 | 4/2006 | Brover |
| 2006/0199155 | A1 | 9/2006 | Mosher |
| 2010/0042438 | A1 | 2/2010 | Moore |
| 2010/0070455 | A1 | 3/2010 | Halperin |
| 2010/0136508 | A1 | 6/2010 | Zekhtser |
| 2013/0261183 | A1 | 10/2013 | Bhagat |
| 2015/0161355 | A1 | 6/2015 | Karra |
| 2015/0356885 | A1 | 12/2015 | Chen |
| 2016/0225284 | A1 | 8/2016 | Schoen |
| 2018/0308389 | A1 | 10/2018 | Moser |
| 2019/0074080 | A1 | 3/2019 | Appelbaum |
| 2019/0221303 | A1 | 7/2019 | Bennett |
| 2019/0251861 | A1 | 8/2019 | Wolf |
| 2020/0138362 | A1 | 5/2020 | Koumpan |

FOREIGN PATENT DOCUMENTS

| | | |
|---|---|---|
| WO | 2014015378 | 1/2014 |
| WO | 2019054737 | 3/2019 |
| WO | 2019110412 | 6/2019 |
| WO | 2019229753 | 12/2019 |

OTHER PUBLICATIONS

Title: Biomarkers of Nutrition and Health: New Tools for New Approaches; Nutrients vol. 11 Issue: 5 Article No. 1092 Published: May 2019; By: Pico, Catalina.

Title: Role of Personalized Nutrition in Chronic-Degenerative Diseases; Nutrients vol. 11 Issue: 8 Article No. 1707 Published: Aug. 2019 DOI: 10.3390/nu11081707; By: Di Renzo, Laura.

* cited by examiner

SYSTEM AND METHOD FOR GENERATING A NEONATAL DISORDER NOURISHMENT PROGRAM

FIELD OF THE INVENTION

The present invention generally relates to the field of artificial intelligence. In particular, the present invention is directed to a system and method for generating a neonatal disorder nourishment program.

BACKGROUND

Current edible suggestion systems do not account for the status of a newborn. This leads to inefficiency of a poor nutrition plan for the newborn. This is further complicated by a lack of uniformity of nutritional plans, which results in poor developmental growth.

SUMMARY OF THE DISCLOSURE

In an aspect, a system for generating a neonatal disorder nourishment program includes a computing device, the computing device configured to obtain a neonatal indicator element, identify a neonatal bundle as a function of the neonatal indicator element, produce a neonatal profile as a function of the neonatal bundle, wherein producing further comprises obtaining a neonatal functional goal as a function of the neonatal bundle, receiving a neonatal recommendation as a function of a neonatal database, and producing the neonatal profile as a function of the neonatal functional goal and neonatal recommendation using a neonatal machine-learning model, determine an aliment as a function of the neonatal profile, and generate a nourishment program as a function of the aliment.

In another aspect, a method for generating a neonatal disorder nourishment program includes obtaining, by a computing device, a neonatal indicator element, identifying, by the computing device, a neonatal bundle as a function of the neonatal indicator element, producing, by the computing device, a neonatal profile as a function of the neonatal bundle, wherein producing further comprises obtaining a neonatal functional goal as a function of the neonatal bundle, receiving a neonatal recommendation as a function of a neonatal database, and producing the neonatal profile as a function of the neonatal functional goal and neonatal recommendation using a neonatal machine-learning model, determining, by the computing device, an aliment as a function of the neonatal profile, and generating, by the computing device, a nourishment program as a function of the aliment.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a nourishment program for neonatal disorders. In an embodiment, this disclosure may obtain one or more neonatal indicator elements that relate to an infant. Aspects of the present disclosure can be used to produce a neonatal profile for an infant that may include identifying a neonatal disorder. Aspects of the present disclosure can also be used to determine an aliment for the neonatal disorder. Aspects of the present disclosure allow for generating a nourishment program. Exemplary embodiments illustrating aspects of the present disclosure are described below in the context of several specific examples.

Figure 1:
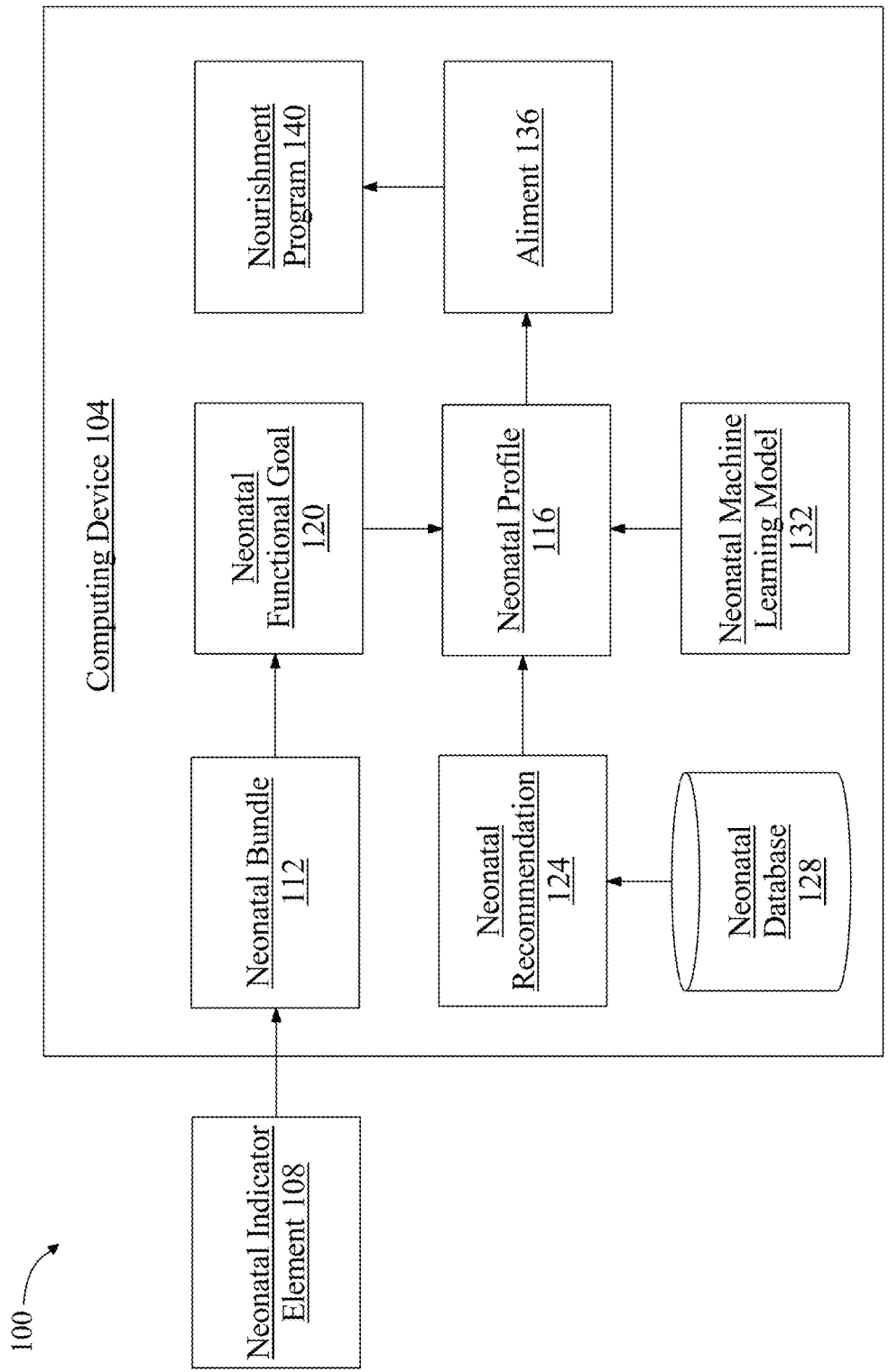
FIG. 1 is a block diagram illustrating an exemplary embodiment of a system for generating a neonatal disorder nourishment program.

Referring now to FIG. 1, an exemplary embodiment of a system 100 for generating a neonatal disorder nourishment program is illustrated. System includes a computing device 104. computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. computing device 104 may include a single computing device operating independently, or may include two or more computing device operating in concert, in parallel, sequentially or the like; two or more computing devices may be included together in a single computing device or in two or more computing devices. computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. computing device 104 may distribute one or more computing tasks as described below across a plurality of computing devices of computing device, which may operate in parallel, in series, redundantly, or in any other manner used for distribution of tasks or memory between computing devices. computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 obtains a neonatal indicator element 108. As used in this disclosure a "neonatal indicator element" is an element of data that denotes a health status of an infant, wherein a health status is a measurement of the relative level of health of an infant. Neonatal indicator element 108 may include a biological sample. As used in this disclosure a "biological sample" is one or more biological specimens collected from an infant. Biological sample may include, without limitation, exhalate, blood, sputum, urine, saliva, feces, semen, and other bodily fluids, as well as tissue. Neonatal indicator element 108 may include a biological sampling device. Neonatal indicator element 108 may include one or more biomarkers. As used in this disclosure a "biomarker" is a molecule and/or chemical that identifies the health status of an infant. As a non-limiting example, biomarkers may include, bilirubin, poptosis regulator BCL2, breast cancer type I susceptibility protein (BRCA1), Fanconi anemia complementation group C (FANCC), vascular endothelial growth factor A (VEGFA), anti-PCNA, anti-SmD, anti-Ro/SSA60, anti-Ro/SSA52, anti-La/SSB, anti-RNPC, S100B, ubiquitin carboxy-terminal hydrolase-L1 [UCH-L1], total Tau, neuron specific enolase, [IL]-1β, IL-6, IL-8, IL-10, IL-12P70, IL-13, interferon-gamma [IFN-γ], tumor necrosis factor alpha [INF-α], brain-derived neurotrophic factor [BNF], monocyte chemoattractant protein-1, and the like thereof. As a further non-limiting example, neonatal indicator element 108 may include datum from one or more devices that collect, store, and/or calculate one or more lights, voltages, currents, sounds, chemicals, pressures, and the like thereof that may be capable of monitoring an infant's health status. As a non-limiting example, neonatal indicator element 108 may be obtained as a function of a baby monitor. As a further non-limiting example, neonatal indicator element 108 may be obtained as a function of a baby monitor with a sensing capability. As used in this disclosure a "sensing capability" is one or more capabilities that monitor the health status of an infant. For example, and without limitation sensing capability may include one or more sleep monitoring capabilities, breathing monitoring capabilities, growth tracking capabilities, and the like thereof. Neonatal indicator element 108 may be received as a function of an infant organ system. As used in this disclosure an "infant organ system" is a group of organs and/or tissues that work together as a biological system. For example, and without limitation, an infant organ system may include one or more respiratory systems, digestive systems, excretory systems, circulatory systems, urinary systems, integumentary systems, skeletal systems, muscular systems, endocrine systems, lymphatic systems, nervous systems, reproductive systems, and the like thereof.

Still referring to FIG. 1, computing device 104 may obtain neonatal indicator element 108 by receiving an input from a user. As used in this disclosure "input" is an element of datum that is obtained as a function of a/an informed advisor, medical advisor, physician, nurse, family member, third-party and the like thereof. As used in this disclosure "informed advisor" is an individual that is skilled in a particular area relating to the study of the infant organ system. As a non-limiting example input may include a nurse entering input that the infant's skin was turning yellow. As a further non-limiting example, input may include a physician entering input that the infant is not vocalizing and/or crying when being stimulated. As a further non-limiting example, inputs may include one or more inputs associated with fussiness, decreased level of consciousness, abnormal movements, feeding difficulty, changes in body temperature, rapid changes in head size, changes in muscle tone, and the like thereof. Input may include one or more inputs from a function of a medical assessment, wherein a "medical assessment" is an evaluation and/or estimation of the health status of an infant. As a non-limiting example medical assessment may include a/an encephalographic measurement, magnetic resonance image, computed tomographic image, electroencephalogram measurement, electromyographic measurement, Apgar test, Guthrie test, tandem mass spectrometric measurement, nuclear medicine renal scan, gene test, and the like thereof.

Still referring to FIG. 1, computing device 104 identifies a neonatal bundle 112 as a function of neonatal indicator element 108. As used in this disclosure a "neonatal bundle" is a group of neonatal indicator elements that relate to one or more functions of the organ systems of an infant. As a non-limiting example, neonatal bundle 112 may include a medical bundle. As used in this disclosure a "medical bundle" is a bundle of neonatal indicator elements that relate to a medical condition. For example, and without limitation medical bundle may include blood conditions, complex birth defects, genetic conditions, central nervous system conditions, gastrointestinal conditions, heart conditions, metabolic conditions, renal conditions, respiratory conditions, and the like thereof. As a non-limiting example, neonatal bundle 112 may include a surgical bundle. As used in this disclosure a "surgical bundle" is a bundle of neonatal indicator elements that relate to a condition that may require surgery. For example, and without limitation surgical bundle may include airway surgical conditions, gastrointestinal surgical conditions, neurosurgical conditions, orthopedic surgical conditions, urological surgical conditions, and the like thereof.

Still referring to FIG. 1, computing device 104 produces a neonatal profile 116 as a function of neonatal bundle 112. As used in this disclosure a "neonatal profile" is a profile of the health status of an infant, wherein a health status is a relative level of wellness and illness of the infant as described above in detail. As a non-limiting example neonatal profile 116 may include a profile comprising a birth weight, Apgar score, neonatal length, and the like thereof. As a further non-limiting example, neonatal profile 116 may include a profile comprising birth weight, congenital anomalies, perinatal problems, and the like thereof. In an embodiment, and without limitation, neonatal profile may include a aliment intolerance. As used in this disclosure an "aliment intolerance" is a difficulty digesting a particular aliment. For example, and without limitation, aliment intolerance may include one or more sensitivities to lactose, gluten, caffeine, salicylates, amines, FODMAPs, sulfites, fructose, aspartame, eggs, MSG, food colorings, yeast, sugar alcohols, and the like thereof. As a further non-limiting example, an aliment intolerance may be a result of an infant lacking an enzyme needed to digest an aliment and/or absorb nutrients from an aliment. Computing device 104 produces neonatal profile 116 by obtaining a neonatal functional goal 120 as a function of neonatal bundle 112. As used in this disclosure "neonatal functional goal" is an intended function of a neonatal bundle. For example, and without limitation neonatal functional goal 120 may include an intended goal of improving function of a circulatory system blood pressure to be enhanced and/or raised. As a further non-limiting example, neonatal functional goal 120 may include an intended goal of improving function of a respiratory system to include enhancing and/or raising a breathing rate of an infant. As a further non-limiting example, neonatal functional goal 120 may include an intended goal of improving function of a urinary system to enhance the filtration rate of an infant.

Still referring to FIG. 1, computing device 104 produces neonatal profile 116 by receiving a neonatal recommendation 124. As used in this disclosure a "neonatal recommendation" is a recommendation and/or guideline associated with a health status of an infant. As a non-limiting example, neonatal recommendation 124 may include one or more recommendations and/or guidelines as a function of improving the health status of an infant. As a further non-limiting example, neonatal recommendation 124 may include one or more recommendations and/or guidelines as a function of maintaining a present health status of an infant. As a non-limiting example, neonatal recommendation 124 may include a recommendation that an Apgar Test be greater than 7. As a further non-limiting example, neonatal recommendation 124 may include a recommendation that bilirubin concentrations be less than 5.2 mg/dL. Neonatal recommendation 124 is received as a function of a neonatal database 128. As used in this disclosure a "neonatal database" is a database of recommendations associated with the health status of an infant. In an embodiment, and without limitation, neonatal database 128 may include information from a peer review, an advisor association, a medical website, and the like thereof. As a non-limiting example, integumentary database 128 may include information from one or more articles and/or publications from the Journal of Neonatology, Journal of Neonatal Nursing, Advances in Neonatal care, and the like thereof. As a non-limiting example, integumentary database 128 may include information from one or more advisor associations such as, but not limited to, the National Association of Neonatal Nurses, The Organization for Neonatal Nurses, Academy of Neonatal Nursing, Association of Women's Health, Obstetric, and Neonatal Nurses. As a further non-limiting example, neonatal recommendation 124 may include one or more recommendations from the World Health Organization. As a non-limiting example, World Health Organization may recommend that serum ferritin concentrations should exceed 150 ug/dL. As a further non-limiting example, World Health Organization may recommend that IL-6 concentrations should be less than 18.3 pg/mL. As a further non-limiting example, neonatal recommendation 124 may include a glomerular filtration rate of 20 mL/min/1.73 m$^2$. As a further non-limiting example, neonatal recommendation 124 may include a systolic pressure of 64 mmHg and a diastolic pressure of 41 mmHg. As a further non-limiting example, neonatal recommendation 124 may include of 40 breaths per minute.

Still referring to FIG. 1, computing device 104 produces neonatal profile 116 as a function of neonatal functional goal 120 and neonatal recommendation 124 using a neonatal machine-learning model 132. As used in this disclosure "neonatal machine-learning model" is a machine-learning model to produce a neonatal profile output given neonatal functional goals and neonatal recommendations as inputs; this is in contrast to a non-machine learning software program where the commands to be executed are determined in advance by a user and written in a programming language. Neonatal machine-learning model 132 may include one or more neonatal machine-learning processes such as supervised, unsupervised, or reinforcement machine-learning processes that computing device 104 and/or a remote device may or may not use in the determination of neonatal profile 116. As used in this disclosure "remote device" is an external device to computing device 104. An neonatal machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train neonatal machine-learning process as a function of a neonatal training set. As used in this disclosure "neonatal training set" is a training set that correlates a neonatal functional goal and/or neonatal recommendation to a neonatal profile. For example, and without limitation, a neonatal functional goal of reducing bilirubin concentration and a neonatal recommendation of a bilirubin concentration to be less than 18.3 pg/mL may relate to a neonatal profile of obstructed bile duct. Neonatal training set may be received as a function of user-entered valuations of neonatal functional goals, neonatal recommendations, and/or neonatal profiles. Computing device 104 may receive neonatal training set by receiving correlations of neonatal functional goals, and/or neonatal recommendations that were previously received and/or determined during a previous iteration of determining neonatal profiles. Neonatal training set may be received by one or more remote devices that at least correlate a neonatal functional goal and/or neonatal recommendation to a neonatal profile, wherein a remote device is an external device to computing device 104, as described above. Neonatal training set may be received in the form of one or more user-entered correlations of a neonatal functional goal and/or neonatal recommendation to a neonatal profile. A user may include an informed advisor, wherein an informed advisor may include, without limitation, neonatologists, pediatricians, family physicians, and the like thereof.

Still referring to FIG. 1, computing device 104 may receive neonatal machine-learning model from a remote device that utilizes one or more neonatal machine learning processes, wherein a remote device is described above in detail. For example, and without limitation, a remote device may include a computing device, external device, processor, and the like thereof. Remote device may perform the neonatal machine-learning process using the neonatal training set to generate neonatal profile 116 and transmit the output to computing device 104. Remote device may transmit a signal, bit, datum, or parameter to computing device 104 that at least relates to neonatal profile 116. Additionally or alternatively, the remote device may provide an updated machine-learning model. For example, and without limitation, an updated machine-learning model may be comprised of a firmware update, a software update, a neonatal machine-learning process correction, and the like thereof. As a non-limiting example a software update may incorporate a new neonatal functional goal that relates to a modified neonatal recommendation. Additionally or alternatively, the updated machine learning model may be transmitted to the remote device, wherein the remote device may replace the neonatal machine-learning model with the updated machine-learning model and determine the neonatal profile as a function of the neonatal functional goal using the updated machine-learning model. The updated machine-learning model may be transmitted by the remote device and received by computing device 104 as a software update, firmware update, or corrected neonatal machine-learning model. For example, and without limitation neonatal machine-learning model may utilize a random forest machine-learning process, wherein the updated machine-learning model may incorporate a gradient boosting machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

In an embodiment and without limitation, neonatal machine-learning model 132 may include a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 may identify neonatal profile 116 by identifying a neonatal disorder. As used in this disclosure an "neonatal disorder" is an ailment and/or collection of ailments that impact an infant's organ system. As a non-limiting example, neonatal disorder may include Hyperbilirubinemia, jaundice, thrombocytopenia, hypoxic ischemic encephalopathy, seizures, head/body cooling, hypotonia, muscle disorders, feeding intolerance, GERD, failure to thrive, anemia of prematurity, apnea of prematurity, atrial septal defect, atrioventricular septal defect, benign neonatal hemangiomatosis, brachial plexus injury, bronchopulmonary dysplasia, cerebral palsy, coarctation of the aorta, congenital adrenal hyperplasia, congenital diaphragmatic hernia, congenital heart disease, diffuse neonatal hemangiomatosis, encephalocele, gastroschisis, hemolytic disease of the newborn, lissencephaly, omphalocele, patent ductus arteriosus, perinatal asphyxia, periventricular leukomalacia, persistent pulmonary hypertension of the newborn, persistent truncus arteriosus, pulmonary hypoplasia, retinopathy of prematurity, spina bifida, spinal muscular atrophy, supraventricular tachycardia, tetralogy of Fallot, tracheoesophageal fistula, tricuspid atresia, trisomy 13/18/21, ventricular septal defects, and the like thereof. Neonatal disorder may be determined as a function of one or more disorder machine-learning models. As used in this disclosure, a "disorder machine-learning model" is a machine-learning model to produce a neonatal disorder output given neonatal indicator element 108 and/or neonatal bundle 112 as inputs; this is in contrast to a non-machine learning software program where the commands to be executed are determined in advance by a user and written in a programming language. Disorder machine-learning model may include one or more disorder machine-learning processes such as supervised, unsupervised, or reinforcement machine-learning processes that computing device 104 and/or a remote device may or may not use in the determination of neonatal disorder. A disorder machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train disorder machine-learning process as a function of a disorder training set. As used in this disclosure, a "disorder training set" is a training set that correlates at least a neonatal enumeration and an infant organ system effect to a neonatal disorder. As used in this disclosure, an "neonatal enumeration" is a measurable value associated with the neonatal indicator element. As used in this disclosure, an "neonatal system effect" is an impact and/or effect the neonatal bundle has on the neonatal system of an infant. As a non-limiting example a neonatal enumeration of 23 may be relate to a neonatal system effect of blood in bowel movements wherein a neonatal disorder of necrotizing enterocolitis may be determined. The disorder training set may be received as a function of user-entered valuations of neonatal enumerations, neonatal system effects, and/or neonatal disorders. Computing device 104 may receive disorder training set by receiving correlations of neonatal enumerations and/or neonatal system effects that were previously received and/or determined during a previous iteration of determining neonatal disorders. The disorder training set may be received by one or more remote devices that at least correlate a neonatal enumeration and/or neonatal system effect to a neonatal disorder, wherein a remote device is an external device to computing device 104, as described above. The disorder training set may be received in the form of one or more user-entered correlations of a neonatal enumeration and neonatal system effect to a neonatal disorder. Additionally or alternatively, a user may include an informed advisor, wherein an informed advisor may include, without limitation, neonatologists, pediatricians, family physicians, and the like thereof.

Still referring to FIG. 1, computing device 104 may receive disorder machine-learning model from the remote device that utilizes one or more disorder machine learning processes, wherein a remote device is described above in detail. For example, and without limitation, a remote device may include a computing device, external device, processor, and the like thereof. The remote device may perform the disorder machine-learning process using the disorder training set to generate neonatal disorder and transmit the output to computing device 104. The remote device may transmit a signal, bit, datum, or parameter to computing device 104 that at least relates to neonatal disorders. Additionally or alternatively, the remote device may provide an updated machine-learning model. For example, and without limitation, an updated machine-learning model may be comprised of a firmware update, a software update, a disorder machine-learning process correction, and the like thereof. As a non-limiting example a software update may incorporate a new neonatal enumeration that relates to a modified neonatal system effect. Additionally or alternatively, the updated machine learning model may be transmitted to the remote device, wherein the remote device may replace the disorder machine-learning model with the updated machine-learning model and determine the neonatal disorder as a function of the neonatal enumeration using the updated machine-learning model. The updated machine-learning model may be transmitted by the remote device and received by computing device 104 as a software update, firmware update, or corrected disorder machine-learning model. For example, and without limitation disorder machine-learning model may utilize a Naïve bayes machine-learning process, wherein the updated machine-learning model may incorporate decision tree machine-learning process.

Still referring to FIG. 1, computing device 104 determines an aliment 136 as a function of neonatal profile 116. As used in this disclosure an "aliment" is a source of nourishment that may be provided to an infant such that the infant may absorb the nutrients from the source. For example and without limitation, an aliment may include formula, breast-milk, dissolved foods, nutrient mixtures, and the like thereof. Computing device 104 may determine aliment 136 as a function of receiving a nourishment composition. As used in this disclosure a "nourishment composition" is a list and/or compilation of all of the nutrients contained in an aliment. As a non-limiting example nourishment composition may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition may be obtained as a function of an aliment directory, wherein an "aliment directory" is a database of aliments that may be identified as a function of one or more neonatal indicator elements, as described in detail below, in reference to FIG. 3.

Still referring to FIG. 1, computing device 104 may produce a nourishment demand as a function of neonatal profile 116. As used in this disclosure a "nourishment demand" is requirement and/or necessary amount of nutrients required for an infant to receive. As a non-limiting example, nourishment demand may include an infant requirement of 9 kcal of lipids to be consumed per day. Nourishment demand may be determined as a function of receiving a nourishment goal. As used in this disclosure a "nourishment goal" is a recommended amount of nutrients that an infant should consume. Nourishment goal may be identified by one or more organizations that relate to, represent, and/or study neonatal conditions, such as the National Association of Neonatal Nurses, The Organization for Neonatal Nurses, Academy of Neonatal Nursing, Association of Women's Health, Obstetric, and Neonatal Nurses, and the like thereof.

Still referring to FIG. 1, computing device 104 may determine aliment 136 as a function of nourishment composition, nourishment demand, and an aliment machine-learning model. As used in this disclosure a "aliment machine-learning model" is a machine-learning model to produce an aliment output given nourishment compositions and nourishment demands as inputs; this is in contrast to a non-machine learning software program where the commands to be executed are determined in advance by a user and written in a programming language. Aliment machine-learning model may include one or more aliment machine-learning processes such as supervised, unsupervised, or reinforcement machine-learning processes that computing device 104 and/or a remote device may or may not use in the determination of aliment 136, wherein a remote device is an external device to computing device 104 as described above in detail. An aliment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train aliment machine-learning process as a function of an aliment training set. As used in this disclosure an "aliment training set" is a training set that correlates at least nourishment composition and nourishment demand to an aliment. For example, and without limitation, nourishment composition of 8 g of protein and a nourishment demand of 4 g/kg of protein as a function of neonatal anemia may relate to an aliment of fortified milk. The aliment training set may be received as a function of user-entered valuations of nourishment compositions, nourishment demands, and/or aliments. Computing device 104 may receive aliment training set by receiving correlations of nourishment compositions and/or nourishment demands that were previously received and/or determined during a previous iteration of determining aliments. The aliment training set may be received by one or more remote devices that at least correlate a nourishment composition and nourishment demand to an aliment, wherein a remote device is an external device to computing device 104, as described above. Aliment training set may be received in the form of one or more user-entered correlations of a nourishment composition and/or nourishment demand to an aliment. Additionally or alternatively, a user may include an informed advisor, wherein an informed advisor may include, without limitation, dermatologists, functional medicine practitioners, chemical pathologists, family physicians, family physicians, and the like thereof. Additionally or alternatively, aliment machine-learning model 148 may identify aliment 136 as a function of one or more classifiers, wherein classifiers are described above in detail.

Still referring to FIG. 1, computing device 104 may receive aliment machine-learning model 148 from a remote device that utilizes one or more aliment machine learning processes, wherein remote device is described above in detail. For example, and without limitation, remote device may include a computing device, external device, processor, and the like thereof. Remote device may perform the aliment machine-learning process using the aliment training set to generate aliment 136 and transmit the output to computing device 104. Remote device may transmit a signal, bit, datum, or parameter to computing device 104 that at least relates to aliment 136. Additionally or alternatively, the remote device may provide an updated machine-learning model. For example, and without limitation, an updated machine-learning model may be comprised of a firmware update, a software update, an aliment machine-learning process correction, and the like thereof. As a non-limiting example a software update may incorporate a new nourishment composition that relates to a modified nourishment demand. Additionally or alternatively, the updated machine learning model may be transmitted to the remote device, wherein the remote device may replace the aliment machine-learning model with the updated machine-learning model and determine the aliment as a function of the nourishment demand using the updated machine-learning model. The updated machine-learning model may be transmitted by the remote device and received by computing device 104 as a software update, firmware update, or corrected aliment machine-learning model. For example, and without limitation an aliment machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

With continued reference to FIG. 1, computing device 104 may be configured to determine a neonatal phase 108. A "neonatal phase," as used in this disclosure, is any data describing an infant life stage. An infant life stage may be marked by one or more characteristics of a developing infant. An infant life stage may include a particular time period, such as a day, week, month, year, and the like thereof. During an infant life stage, an infant may modify and/or develop one or more biomedical, behavioral, and/or social developments, such as motor functions, sounds, cognitive functions and the like thereof. Computing device 104 may calculate neonatal phase by receiving an age datum. An "age datum," as used in this disclosure, is any data that is utilized to calculate neonatal phase. Age datum may describe an infant's life stage development which may be calculated by an informed advisor, wherein an informed advisor is described in detail above. For example, a physician may calculate an infant's life stage development by analyzing a blood analysis from an infant. Age datum may describe an infant's conception date which may indicate a possible range of days during which a user's baby was conceived whether using artificial or natural methods to assist in determining a nutrient requirement as a function of the conception date. For example, a date of conception may reflect a range of days during which sexual intercourse may have led to conception, wherein the date of conception may alter the nutrient demand of the infant. Age datum may describe one or more measurements obtained from an ultrasound such as a fundal height measurement or a size measurement.

With continued reference to FIG. 1, computing device 104 may be configured to classify an age datum to a neonatal progression level. As used in this disclosure a "neonatal progression level" is a level at which the infant should be at in relation to the age datum. For example, and without limitation, age datum may be received that identifies an infant at age 2 months old, wherein the neonatal progression level identifies that the development of the infant is only at 1 month. As a further non-limiting example, age datum may be received that identifies an infant at age 34 weeks old, wherein the neonatal progression level identifies that the development of the infant is 42 weeks old. Computing device 104 may classify age datum to neonatal progression level by generating a neonatal classification algorithm. A "neonatal classification algorithm," as used in this disclosure is any calculation and/or series of calculations that identify to which set of categories or "bins" a new observation or input belongs. Generating neonatal classification algorithm may include generating a machine learning model using a classification algorithm. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. Computing device 104 may utilize neonatal classification model that utilizes age datum as an input and outputs neonatal progression level.

With continued reference to FIG. 1, computing device 104 may be configured to generate a neonatal phase label. A "neonatal phase label," as used in this disclosure, is any textual, numerical, and/or symbolic data that identifies whether age datum belongs to a particular class or not, where a class may include any neonatal progression level and/or neonatal phase. For example, a neonatal phase label may indicate that current age datum belongs to a 36-week neonatal phase label and the age datum does not belong to a 28-week phase, a 1-month phase, a 6-month phase, and the like thereof. Additionally or alternatively, computing device 104 may identify a nourishment delivery component as a function of calculating neonatal phase, wherein a nourishment delivery component is a component that allows for nourishment to be received by an infant, as described below in detail, in reference to FIG. 4.

Still referring to FIG. 1, computing device 104 generates a nourishment program 140 as a function of aliment 136. As used in this disclosure a "nourishment program" is a program consisting of one or more aliments that are to be administered to an infant over a given time period, wherein a time period is a temporal measurement such as seconds, minutes, hours, days, weeks, months, years, and the like thereof. As a non-limiting example nourishment program 140 may consist of recommending a breast milk fortified with calcium for 7 days. As a further non-limiting example nourishment program 140 may recommend formula supplemented with phosphorous for a first day, formula supplemented with sodium for a second day, and breast milk for a third day. In an embodiment, nourishment program 140 may include one or more recommendations of aliments for a mother to consume to alter and/or enhance nourishment compositions of breast milk. As a non-limiting example nourishment program may include one or more recommendations of aliments for a mother to consume, such as recommending salmon to enhance vitamin C and docosahexaenoic acid concentrations in breast milk for the infant. As a further non-limiting example, nourishment program 140 may recommend one or more diet programs such as paleo, keto, vegan, vegetarian, and the like thereof to the mother that is breastfeeding the infant.

In an embodiment, and still referring to FIG. 1, computing device 104 may develop nourishment program 140 as a function of a neonatal outcome. As used in this disclosure a "neonatal outcome" is an outcome that an aliment may generate according to a predicted and/or purposeful plan. As a non-limiting example, neonatal outcome may include a treatment outcome. As used in this disclosure a "treatment outcome" is an intended outcome that is designed to at least reverse and/or eliminate neonatal indicator element 108 associated with neonatal profile 116 and/or neonatal disorder. As a non-limiting example, a treatment outcome may include reversing the effects of the neonatal disorder jaundice. As a further non-limiting example, a treatment outcome includes reversing the neonatal disorder of hydrocephalus. Neonatal outcome may include a prevention outcome. As used in this disclosure a "prevention outcome" is an intended outcome that is designed to at least prevent and/or avert neonatal indicator element 108 associated with neonatal profile 116 and/or neonatal disorder. As a non-limiting example, a prevention outcome may include preventing the development of the neonatal disorder of bradycardia.

Still referring to FIG. 1, computing device 104 may develop nourishment program 140 as a function of aliment 136 and treatment outcome using a nourishment machine-learning model. As used in this disclosure a "nourishment machine-learning model" is a machine-learning model to produce a nourishment program output given aliments and/or neonatal outcomes as inputs; this is in contrast to a non-machine learning software program where the commands to be executed are determined in advance by a user and written in a programming language. Nourishment machine-learning model may include one or more nourishment machine-learning processes such as supervised, unsupervised, or reinforcement machine-learning processes that computing device 104 and/or a remote device may or may not use in the development of nourishment program 140. Nourishment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train nourishment machine-learning process as a function of a nourishment training set. As used in this disclosure a "nourishment training set" is a training set that correlates a neonatal outcome to an aliment. The nourishment training set may be received as a function of user-entered aliments, neonatal outcomes, and/or nourishment programs. For example, and without limitation, a neonatal outcome of treating anemia may correlate to an aliment of iron. Computing device 104 may receive nourishment training by receiving correlations of neonatal outcomes and/or aliments that were previously received and/or determined during a previous iteration of developing nourishment programs. The nourishment training set may be received by one or more remote devices that at least correlate a neonatal outcome and/or aliment to a nourishment program, wherein a remote device is an external device to computing device 104, as described above. Nourishment training set may be received in the form of one or more user-entered correlations of a neonatal outcome and/or aliment to a nourishment program. Additionally or alternatively, a user may include an informed advisor, wherein an informed advisor may include, without limitation, neonatologists, pediatricians, family physicians, and the like thereof.

Still referring to FIG. 1, computing device 104 may receive nourishment machine-learning model from the remote device that utilizes one or more nourishment machine learning processes, wherein a remote device is described above in detail. For example, and without limitation, a remote device may include a computing device, external device, processor, and the like thereof. The remote device may perform the nourishment machine-learning process using the nourishment training set to develop nourishment program 140 and transmit the output to computing device 104. The remote device may transmit a signal, bit, datum, or parameter to computing device 104 that at least relates to nourishment program 140. Additionally or alternatively, the remote device may provide an updated machine-learning model. For example, and without limitation, an updated machine-learning model may be comprised of a firmware update, a software update, a nourishment machine-learning process correction, and the like thereof. As a non-limiting example a software update may incorporate a new neonatal outcome that relates to a modified aliment. Additionally or alternatively, the updated machine learning model may be transmitted to the remote device, wherein the remote device may replace the nourishment machine-learning model with the updated machine-learning model and develop the nourishment program as a function of the neonatal outcome using the updated machine-learning model. The updated machine-learning model may be transmitted by the remote device and received by computing device 104 as a software update, firmware update, or corrected nourishment machine-learning model. For example, and without limitation nourishment machine-learning model may utilize a neural net machine-learning process, wherein the updated machine-learning model may incorporate decision tree machine-learning processes.

Figure 2:
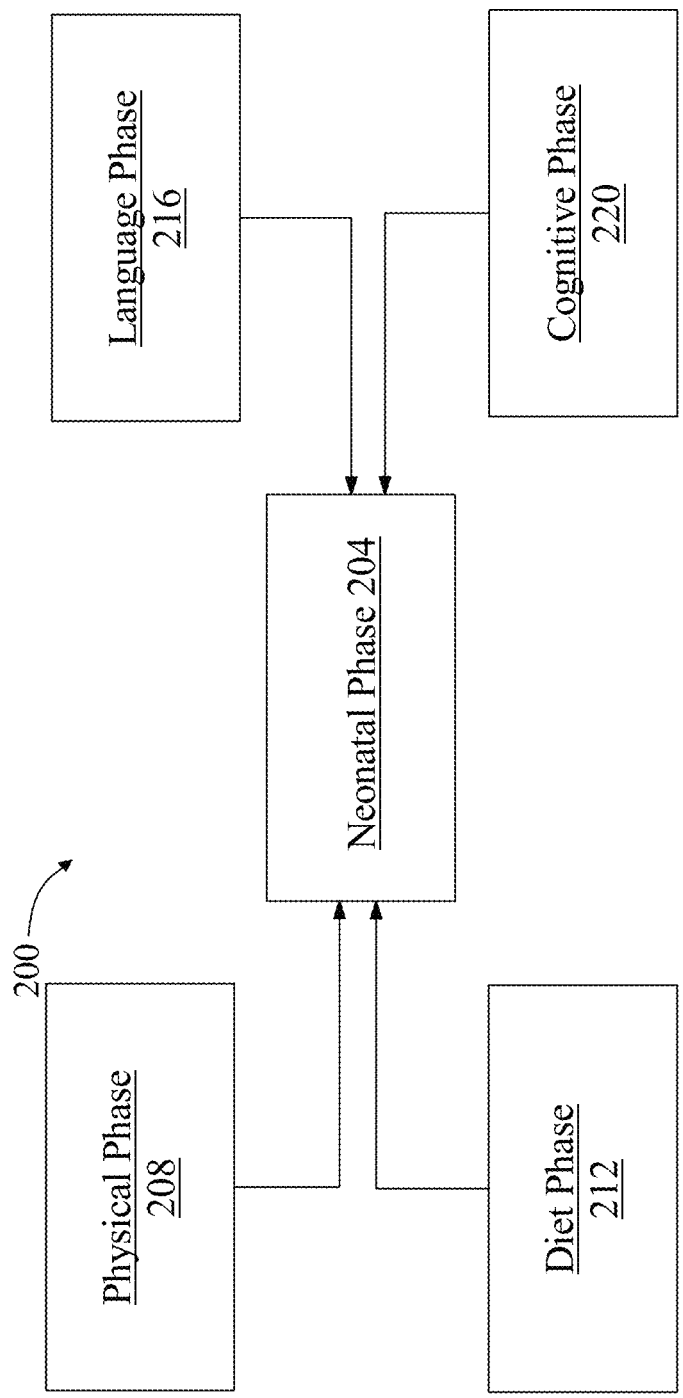
FIG. 2 is a block diagram of an exemplary embodiment of a neonatal phase according to an embodiment of the invention.

Now referring to FIG. 2, an exemplary embodiment 200 of a neonatal phase 204 is illustrated. As used in this disclosure a "neonatal phase" is a phase of development that an infant may or may not progress through. Neonatal phase 204 may include a physical phase 208. As used in this disclosure a "physical phase" is a developmental phase associated with physical milestones that an infant may or may not progress through. For example, and without limitation, physical phase 208 may include one or more actions including lifting their head, holding their head up, holding their head steady, bearing weight on their legs, playing with their hands and feet, and the like thereof. Neonatal phase 204 may include a diet phase 212. As used in this disclosure a "diet phase" is a developmental phase associated with dietary milestones that an infant may or may not progress through. For example, and without limitation, dietary phase 212 may include one or more capabilities to ingest varying aliment types and/or nutrients. In an embodiment, and without limitation, diet phase may include developing from a parenteral administration of nutrients to breast milk. Neonatal phase 204 may include a language phase 216. As used in this disclosure a "language phase" is a developmental phase associated with language milestones that an infant may or may not progress through. For example, and without limitation, language phase 216 may include one or more language milestones such as crying, gurgles, coos, laughs, imitation sounds, jabbers, and the like thereof. Neonatal phase 204 may include a cognitive phase 220. As used in this disclosure a "cognitive phase" is a developmental phase associated with cognitive milestones that an infant may or may not progress through. For example, and without limitation, cognitive phase 220 may include one or more cognitive milestones such as responses to sounds, tracking of movements with the infant's eyes, identification of objects, distinguishment of colors, and the like thereof.

Figure 3:
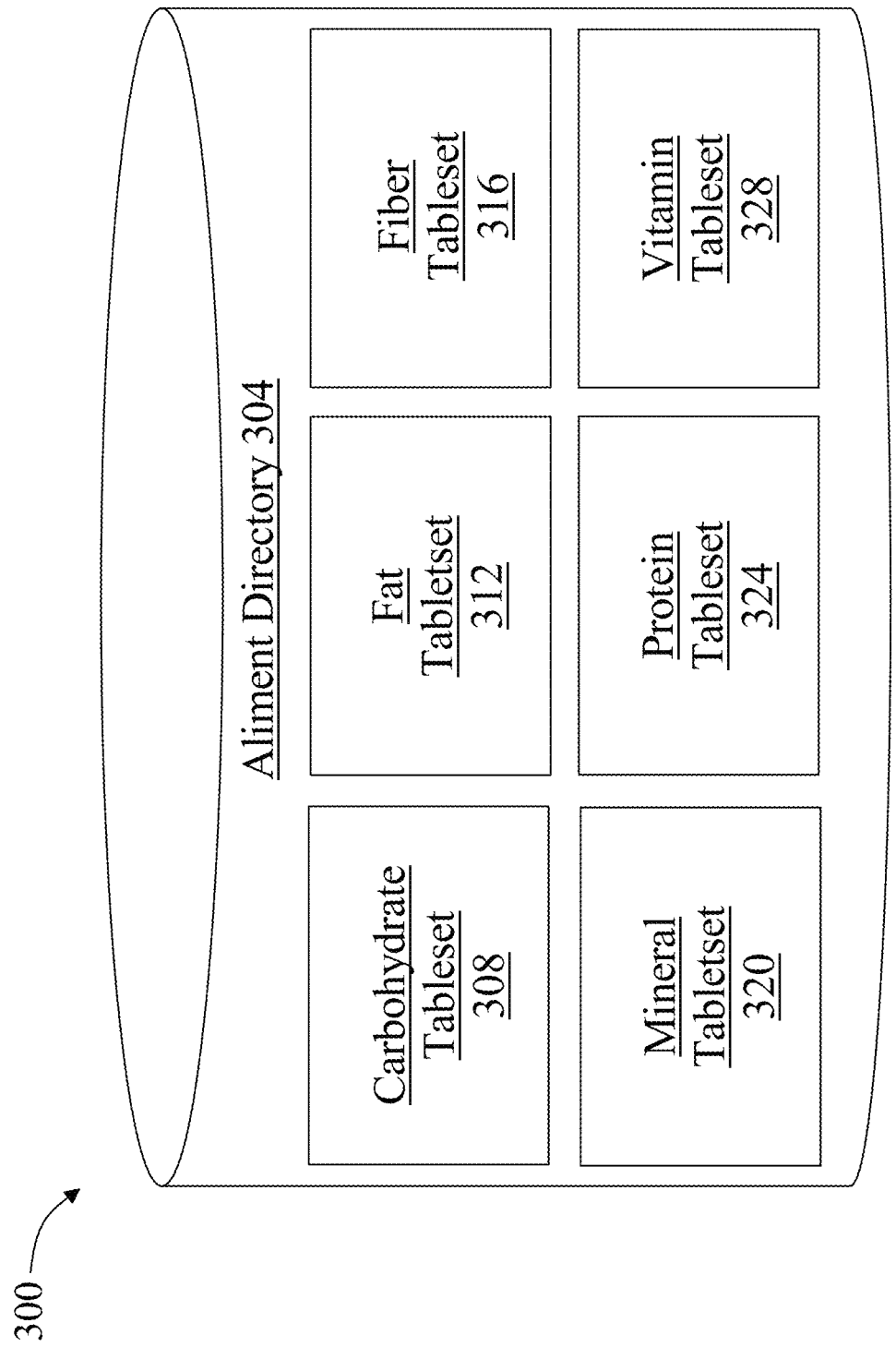
FIG. 3 is a block diagram of an exemplary embodiment of an aliment directory according to an embodiment of the invention.

Now referring to FIG. 3, an exemplary embodiment 300 of an aliment directory 304 according to an embodiment of the invention is illustrated. Aliment directory 304 may be implemented, without limitation, as a relational databank, a key-value retrieval databank such as a NOSQL databank, or any other format or structure for use as a databank that a person skilled in the art would recognize as suitable upon review of the entirety of this disclosure. Aliment directory 304 may alternatively or additionally be implemented using a distributed data storage protocol and/or data structure, such as a distributed hash table or the like. Aliment directory 304 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Aliment directory 304 may include a carbohydrate tableset 308. Carbohydrate tableset 308 may relate to a nourishment composition of an aliment with respect to the quantity and/or type of carbohydrates in the aliment. As a non-limiting example, carbohydrate tableset 308 may include monosaccharides, disaccharides, oligosaccharides, polysaccharides, and the like thereof. Aliment directory 304 may include a fat tableset 312. Fat tableset 312 may relate to a nourishment composition of an aliment with respect to the quantity and/or type of esterified fatty acids in the aliment. Fat tableset 312 may include, without limitation, triglycerides, monoglycerides, diglycerides, phospholipids, sterols, waxes, and free fatty acids. Aliment directory 304 may include a fiber tableset 316. Fiber tableset 316 may relate to a nourishment composition of an aliment with respect to the quantity and/or type of fiber in the aliment. As a non-limiting example, fiber tableset 316 may include soluble fiber, such as beta-glucans, raw guar gum, psyllium, inulin, and the like thereof as well as insoluble fiber, such as wheat bran, cellulose, lignin, and the like thereof. Aliment directory 304 may include a mineral tableset 320. Mineral tableset 320 may relate to a nourishment composition of an aliment with respect to the quantity and/or type of minerals in the aliment. As a non-limiting example, mineral tableset 320 may include calcium, phosphorous, magnesium, sodium, potassium, chloride, sulfur, iron, manganese, copper, iodine, zing, cobalt, fluoride, selenium, and the like thereof. Aliment directory 304 may include a protein tableset 324. Protein tableset 324 may relate to a nourishment composition of an aliment with respect to the quantity and/or type of proteins in the aliment. As a non-limiting example, protein tableset 324 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Aliment directory 304 may include a vitamin tableset 328. Vitamin tableset 328 may relate to a nourishment composition of an aliment with respect to the quantity and/or type of vitamins in the aliment. As a non-limiting example, vitamin tableset 328 may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Figure 4:
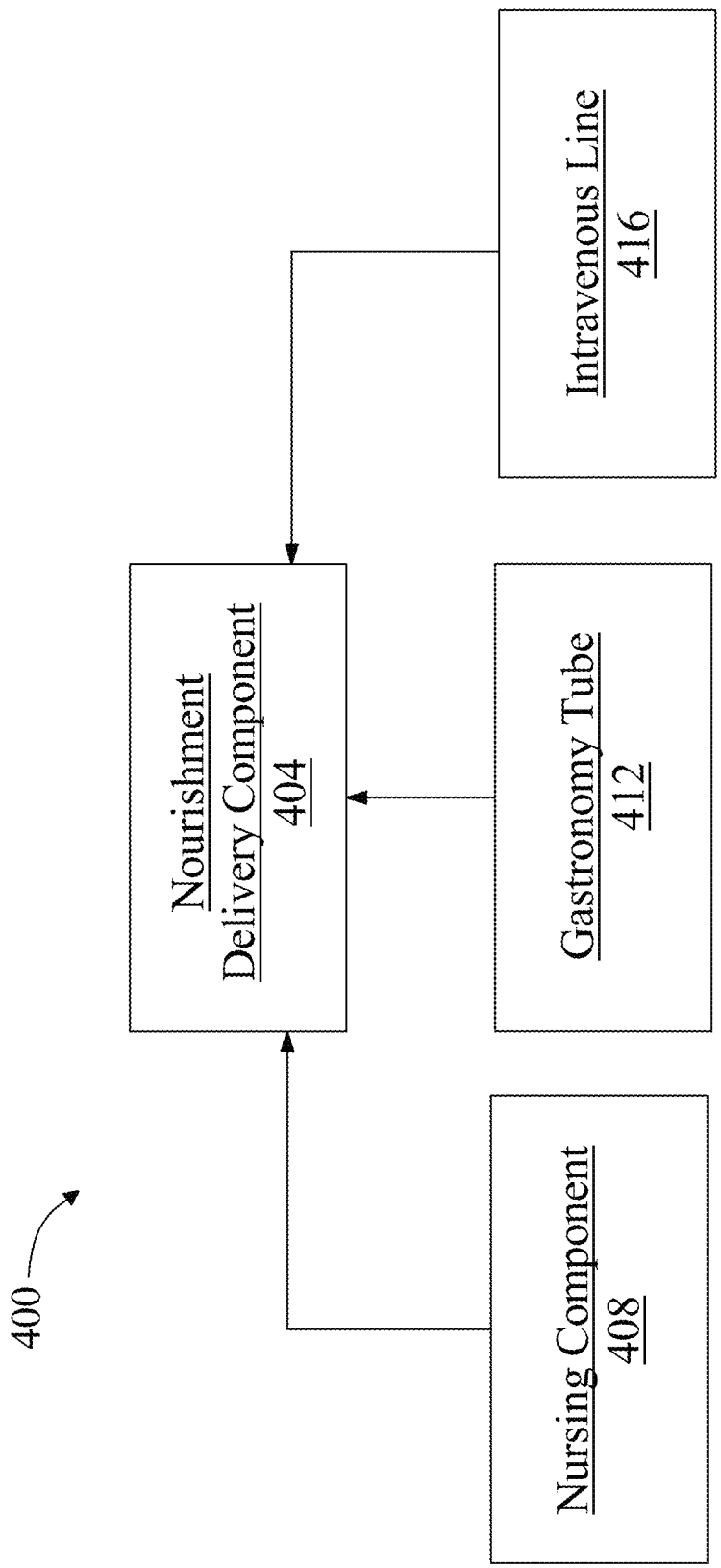
FIG. 4 is a block diagram of an exemplary embodiment of nourishment delivery component according to an embodiment of the invention.

Referring now to FIG. 4, an exemplary embodiment of a nourishment delivery component 404 is illustrated. As used in this disclosure a "nourishment delivery component" is a component that allows for nourishment to be received by an infant. For example, and without limitation, nourishment delivery component may include any component that aids in delivery nutrients and/or sustenance to an infant. Nourishment delivery component 404 may include a nursing component 408. As used in this disclosure a "nursing component" is a component that allows for nourishment to be received by an infant as a function of a nursing mechanism. For example, and without limitation, nursing component 408 may include breast feeding, wet nursing, dry-nursing, and the like thereof. In an embodiment nursing component may include a nutritional recommendation. As used in this disclosure a "nutritional recommendation" is a recommendation for a nursing mother to consume a nutrient to alter and/or modify breast milk. For example, and without limitation, nutritional recommendation may include recommending soybean oil, walnuts, chia, hemp, and/or flax seeds to increase concentration of omega fatty acids in breast milk. As a further non-limiting example nutritional recommendation may include recommending removing dairy and soy products from the mother's diet to reduce the amount of CMPI in breast milk for an infant that has a CMPO aliment intolerance. As a further non-limiting example, nutritional recommendation may include recommending to a nursing mother to reduce exercise frequency to reduce the concentration of lactic acid in the breast milk. In an embodiment, and without limitation, nursing component 408 may include one or more bottle feeding techniques, wherein an aliment of a plurality of aliments are placed within a bottle that is sealed with a nipple extruding from the top of the bottle to allow an infant to suckle and/or nurse from the nipple. Nutritional recommendation may include recommending one or more formulas for a bottle-feeding technique to reduce the effects of an aliment intolerance, wherein an aliment intolerance is a difficulty digesting a particular aliment as described above, in reference to FIG. 1. For example, and without limitation, nutritional recommendation may include recommending a soy-based formula as opposed to a milk based formula to reduce the effects of a lactose intolerance. As a further non-limiting example, nutritional recommendation may include recommending an elemental amino acid-based formula as opposed to a milk-based formula to reduce the effects of a CMPI aliment intolerance. Nourishment delivery component 404 may include a gastronomy tube 412. As used in this disclosure a "gastronomy tube" is a component that allows for nourishment to be received by an infant as a function of a feeding tube. For example, and without limitation, gastronomy tube 412 may include a gavage tube, enteral feeding tube, nasogastric feeding tube, nasojejunal feeding tube, gastrojejunal feeding tube, jejunal feeding tube, and the like thereof. Nourishment delivery component 404 may include an intravenous line 416. As used in this disclosure an "intravenous line" is a component that allows for nourishment to be received by an infant as a function of a parenteral feeding mechanism. For example, and without limitation, intravenous line may include a tube in a vein located within an infant's hand, foot, scalp, belly button, and the like thereof.

Figure 5:
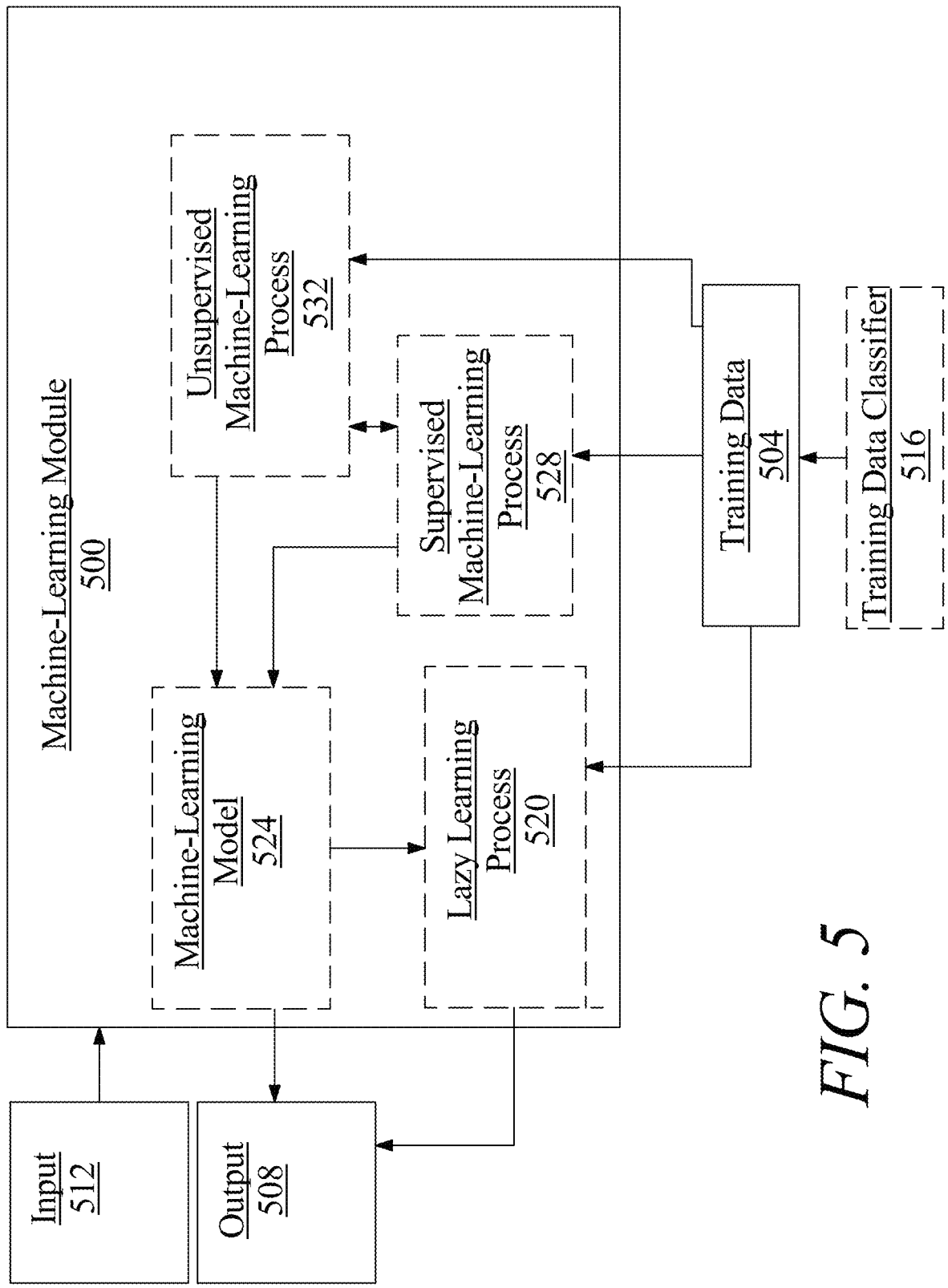
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example inputs include neonatal functional goals and/or neonatal exemplary embodiments may relate to outputs of neonatal profiles.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to sub-categories such as neonatal recommendations relating to one or more organ systems and/or tissue systems of the infant.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include neonatal functional goals and/or neonatal recommendations as described above as inputs, neonatal profiles as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
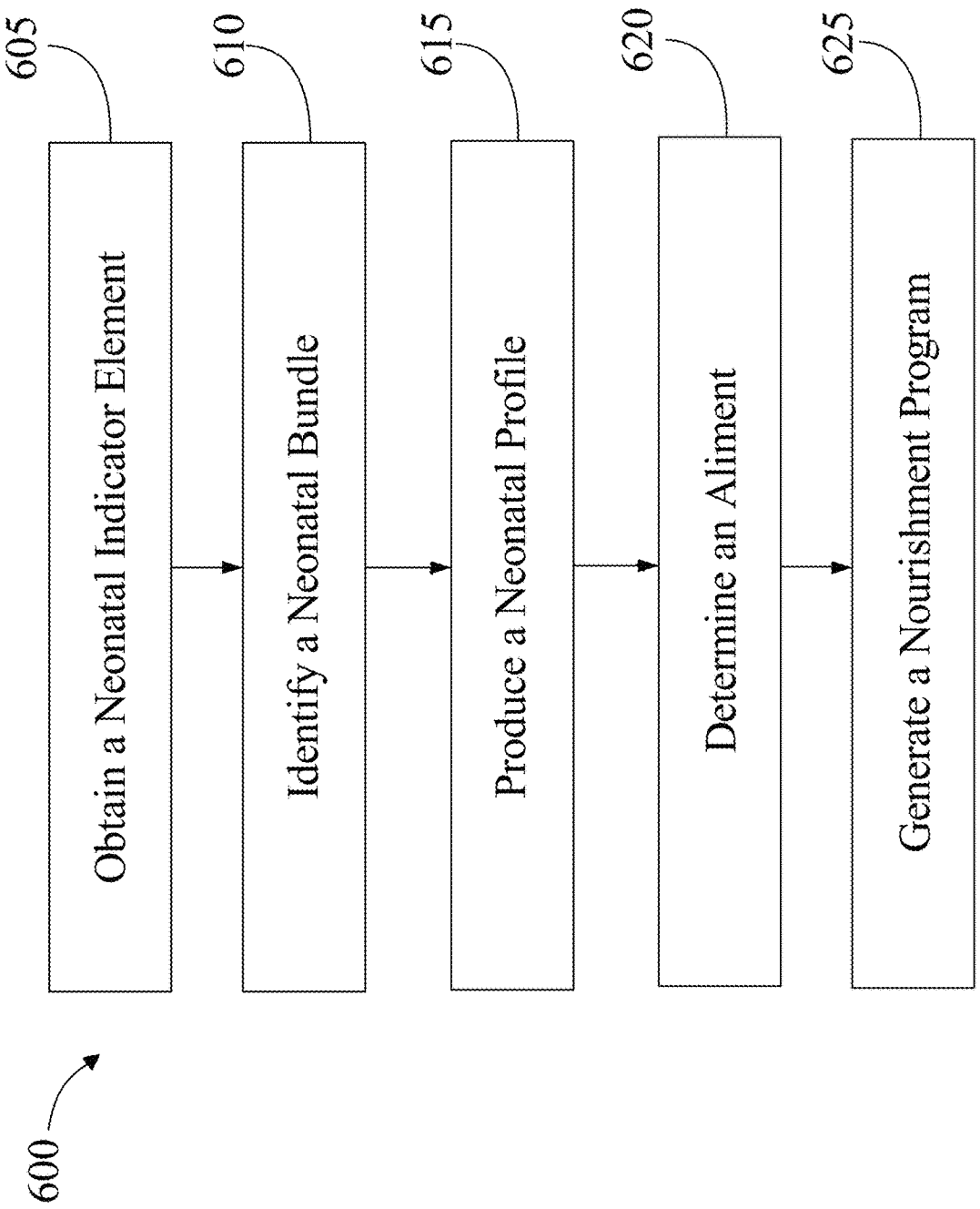
FIG. 6 is a process flow diagram illustrating an exemplary embodiment of a method of generating a neonatal disorder nourishment program.

Now referring to FIG. 6, an exemplary embodiment of a method 600 for generating a neonatal disorder nourishment program is illustrated. At step 605, a computing device 104 obtains a neonatal indicator element 108. Computing device 104 includes any of the computing device 104 as described above, in reference to FIGS. 1-5. Neonatal indicator element 108 includes any of the neonatal indicator element 108 as described above, in reference to FIGS. 1-5.

Still referring to FIG. 6, at step 610, computing device 104 identifies a neonatal bundle 112 as a function of neonatal indicator element 108. Neonatal bundle 112 includes any of the neonatal bundle 112 as described above, in reference to FIGS. 1-5.

Still referring to FIG. 6, at step 615, computing device 104 produces a neonatal profile 116 as a function of neonatal bundle 112. Neonatal profile 116 includes any of the neonatal profile 116 as described above, in reference to FIGS. 1-5. Neonatal profile 116 is produced by obtaining a neonatal functional goal 120. Neonatal functional goal 120 includes any of the neonatal functional goal 120 as described above, in reference to FIGS. 1-5. Neonatal profile 116 is produced by receiving a neonatal recommendation 124. Neonatal recommendation 124 includes any of the neonatal recommendation 124 as described above, in reference to FIGS. 1-5. Neonatal recommendation 124 is received as a function of a neonatal database 128. Neonatal database 128 includes any of the neonatal database 128 as described above, in reference to FIGS. 1-5. Neonatal profile 116 is produced as a function of neonatal functional goal 120 and neonatal recommendation 124 using a neonatal machine-learning model 132. Neonatal machine-learning model 132 includes any of the neonatal machine-learning model 132 as described above, in reference to FIGS. 1-5.

Still referring to FIG. 6, at step 620, computing device 104 determines an aliment 136 as a function of neonatal profile 116. Aliment 136 includes any of the aliment 136 as described above, in reference to FIGS. 1-5.

Still referring to FIG. 6, at step 625, computing device 104 generates a nourishment program 140 as a function of aliment 136. Nourishment program 140 includes any of the nourishment program 140 as described above, in reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
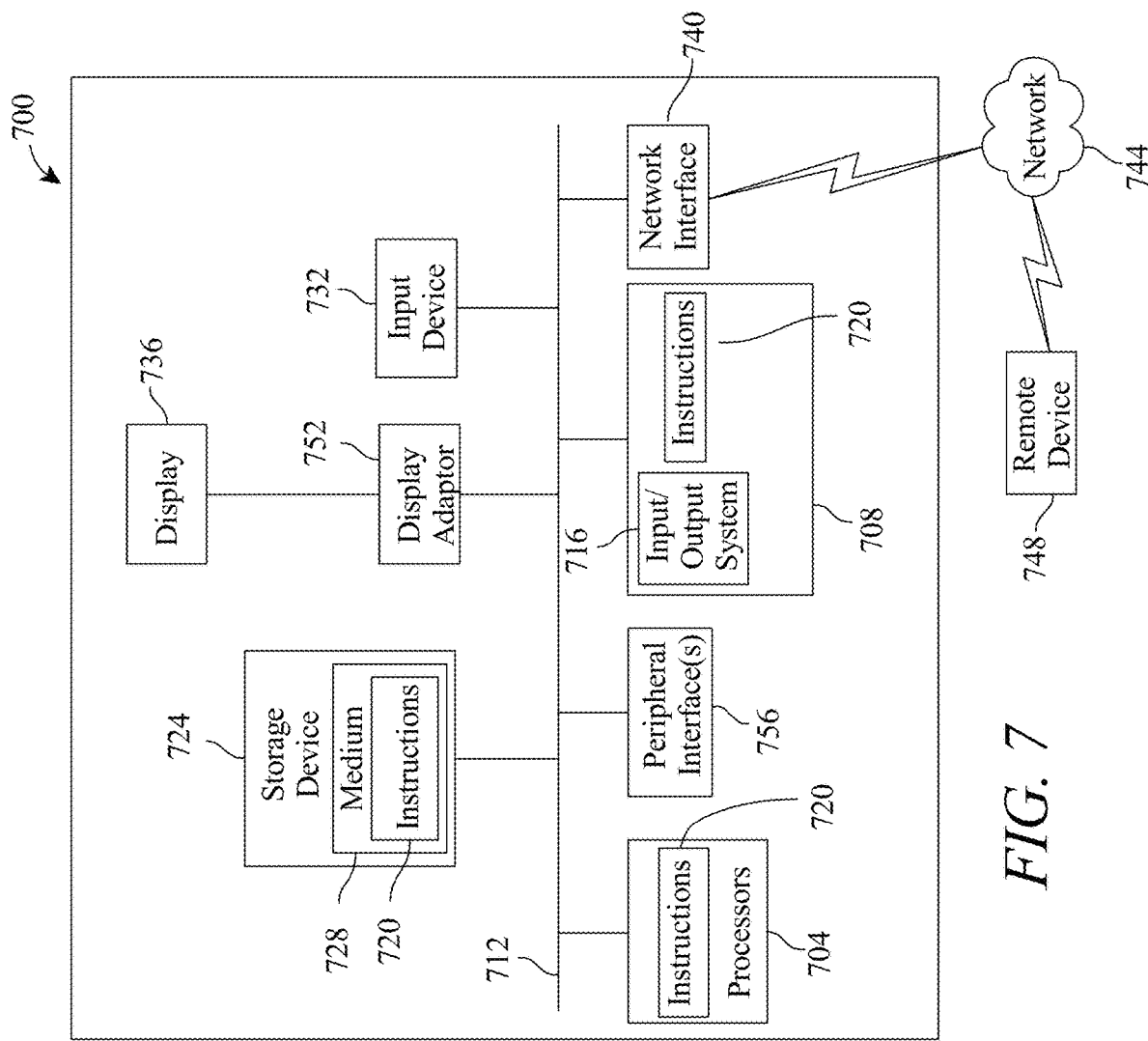
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIRE-WIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a neonatal disorder nourishment program, the system comprising:
 a computing device, the computing device configured to:
  obtain a neonatal indicator element;
  identify a neonatal bundle as a function of the neonatal indicator element;
  produce a neonatal profile of an infant as a function of the neonatal bundle,
   wherein producing the neonatal profile further comprises:
    receiving neonatal training data correlating a plurality of neonatal functional goals and a plurality of neonatal recommendations to the neonatal bundle and the neonatal profiles;
    training a neonatal machine learning model using the neonatal training data;
    inputting the plurality of neonatal functional goals and the plurality of neonatal recommendations to the trained neonatal machine learning model; and
    outputting the neonatal profile from the trained neonatal machine learning model;
  determine an aliment as a function of the neonatal profile; and
  generate a nourishment program as a function of the aliment, wherein the nourishment program comprises a diet program for a mother of the infant.

2. The system of claim 1, wherein the neonatal indicator element includes a biomarker.

3. The system of claim 1, wherein obtaining the neonatal indicator element includes receiving an input from a user and obtaining the neonatal indicator element as a function of the input.

4. The system of claim 1, wherein producing the neonatal profile includes determining a neonatal disorder and producing the neonatal profile as a function of the neonatal disorder.

5. The system of claim 4, wherein determining the neonatal disorder further comprises:
 obtaining a disorder training set; and
 determining the neonatal disorder as a function of the neonatal indicator element using a disorder machine-learning model, wherein the disorder machine-learning model is trained as a function of the disorder training set, wherein the disorder training data set comprises neonatal enumeration inputs and infant organ system effect inputs correlated with neonatal disorder outputs.

6. The system of claim 1, wherein determining the aliment further comprises calculating a neonatal phase, wherein the neonatal phase comprises a cognitive phase.

7. The system of claim 6, wherein calculating the neonatal phase further comprises:
 receiving an age datum;
 classifying the age datum to a neonatal progression level; and
 generating the neonatal phase as a function of the classifying.

8. The system of claim 6, wherein calculating the neonatal phase further comprises identifying a nourishment delivery component.

9. The system of claim 1, wherein determining the aliment further comprises:
 receiving a nourishment composition from an aliment directory;
 producing a nourishment demand as a function of the neonatal profile; and
 determining the aliment as a function of the nourishment composition and the nourishment demand using an aliment machine-learning model.

10. The system of claim 1, wherein generating the nourishment program further comprises:
 receiving a neonatal outcome; and
 generating the nourishment program as a function of the neonatal outcome using a nourishment machine-learning model.

11. A method for generating a neonatal disorder nourishment program, the method comprising:
 obtaining, by a computing device, a neonatal indicator element;
 identifying, by the computing device, a neonatal bundle as a function of the neonatal indicator element;
 producing, by the computing device, a neonatal profile of an infant as a function of the neonatal bundle, wherein producing the neonatal profile further comprises:
  receiving neonatal training data correlating a plurality of neonatal functional goals and a plurality of neonatal recommendations to the neonatal bundle and the neonatal profiles;
  training a neonatal machine learning model using the neonatal training data;
  inputting the plurality of neonatal functional goals and the plurality of neonatal recommendations to the trained neonatal machine learning model; and
  outputting the neonatal profile from the trained neonatal machine learning model;
 determining, by the computing device, an aliment as a function of the neonatal profile; and
 generating, by the computing device, a nourishment program as a function of the aliment wherein the nourishment program comprises a diet program for a mother of the infant.

12. The method of claim 11, wherein the neonatal indicator element includes a biomarker.

13. The method of claim 11, wherein obtaining the neonatal indicator element includes receiving an input from a user and obtaining the neonatal indicator element as a function of the input.

14. The method of claim 11, wherein producing the neonatal profile includes determining a neonatal disorder and producing the neonatal profile as a function of the neonatal disorder.

15. The method of claim 14, wherein determining the neonatal disorder further comprises:
 obtaining a disorder training set; and
 determining the neonatal disorder as a function of the neonatal indicator element using a disorder machine-learning model, wherein the disorder machine-learning model is trained as a function of the disorder training set, wherein the disorder training data set comprises neonatal enumeration inputs and infant organ system effect inputs correlated with neonatal disorder outputs.

16. The method of claim 11, wherein determining the aliment further comprises calculating a neonatal phase, wherein the neonatal phase comprises a cognitive phase.

17. The method of claim 16, wherein calculating the neonatal phase further comprises:
   receiving an age datum;
   classifying the age datum to a neonatal progression level; and
   generating the neonatal phase as a function of the classifying.

18. The method of claim 16, wherein calculating the neonatal phase further comprises identifying a nourishment delivery component.

19. The method of claim 11, wherein determining the aliment further comprises:
   receiving a nourishment composition from an aliment directory;
   producing a nourishment demand as a function of the neonatal profile; and
   determining the aliment as a function of the nourishment composition and the nourishment demand using an aliment machine-learning model.

20. The method of claim 11, wherein generating the nourishment program further comprises:
   receiving a neonatal outcome; and
   generating the nourishment program as a function of the neonatal outcome using a nourishment machine-learning model.

* * * * *